United States Patent [19]

Grisoni et al.

[11] Patent Number: 5,145,933
[45] Date of Patent: Sep. 8, 1992

[54] ORGANOSILOXANE GEL-FORMING COMPOSITIONS AND USE THEREOF

[75] Inventors: Bernard F. R. Grisoni, El Toro, Calif.; David Pocknell, Antibes, France

[73] Assignee: Dow Corning France S.A., Valbonne, France

[21] Appl. No.: 665,855

[22] Filed: Mar. 7, 1991

Related U.S. Application Data

[63] Continuation-in-part of Ser. No. 277,364, Nov. 19, 1988, abandoned.

[51] Int. Cl.$^5$ .............................................. C08G 77/06
[52] U.S. Cl. .................................... 528/15; 528/31; 528/32
[58] Field of Search ............................. 528/31, 32, 15

[56] References Cited

U.S. PATENT DOCUMENTS 3,663,973 5/1972 Spence ................................. 5/348
4,535,141 8/1985 Kroupa .............................. 528/15
4,703,070 10/1987 Locko et al. ...................... 523/102

FOREIGN PATENT DOCUMENTS 2185750A 7/1987 United Kingdom .

Primary Examiner—Melvyn I. Marquis
Assistant Examiner—Karen A. Hellender
Attorney, Agent, or Firm—Robert Spector

[57] ABSTRACT

Non-friable siloxane gels which can be used for gel dressings and in medical prostheses are made from compositions comprising (A) alkenyl-containing polydiorganosiloxanes; (B) hydrosilicon compounds having at least 3 Si-H groups; (C) SiH end-blocked polydiorganosiloxanes and (D) a catalyst. These compositions cure rapidly at room temperature having a ratio (RHAlk) of SiH:Si-Alkenyl of from 3:1 to 20:1, the percentage of silicon-bonded H atoms provided by (C) not being less than $81.36-(3.6 \times RHAlk)$ and having a value of from 10% to 90%.

12 Claims, No Drawings

ORGANOSILOXANE GEL-FORMING COMPOSITIONS AND USE THEREOF

REFERENCE TO RELATED APPLICATIONS

This application is a continuation-in-part of application Ser. No. 07/277,364 filed on Nov. 29, 1988, now abandoned.

This invention relates to a siloxane gel-forming composition and to a non-friable siloxane gel formed by the composition.

Siloxane gels have been known for a long time. They are materials with very little physical strength, for example tear strength, elongation, tensile strength and shore hardness. These materials are neither solid nor liquid and usually flow under pressure They are useful for example for encapsulating electronic components, and in the manufacture of medical prostheses. They have been described for example in G.B. Patent Specification 849 885 and U.S. Specification 4 072 635. The former of these Specifications describes and claims a soft, non-friable gel which is the reaction product of an intimate mixture consisting essentially of (1) an organopolysiloxane having a viscosity of from 100 to 10,000 mm$^2$/s at 25° C. and being a copolymer consisting essentially of units of the general formulae RViSiO, R$_2$SiO and CH$_3$R$_2$SiO$_{0.5}$ where each R is a methyl or phenyl group and Vi is a vinyl group, at least 0.174 molar per cent of the units in said copolymer being the said RViSiO units; (2) a liquid hydrogenosiloxane of the general formula HRCH$_3$SiO(R$_2$SiO)$_n$SiCH$_3$RH where each R is as above defined and n has an average value such that the viscosity of the hydrogenosiloxane is not more than 10,000 mm$^2$/s at 25° C., not more than 25 molar percent in (1) and (2) being phenyl, and (3) a platinum catalyst in specified amounts; the proportions of (1) and (2) being such that prior to the reaction there is an average of from 1.4 to 1.8 of the silicon-bonded hydrogen atoms in (2) per molecule of (1) and there being at least one RViSiO unit in (1) for every silicon-bonded hydrogen atom in (2), the molecular weight of (1) being calculated by a specified equation. The gel-formation reaction is said to take place at room temperature over a typical period of 2 to 6 days, although it is preferred to heat the mixture to a temperature of 125° to 150° C. for about 8 hours, in order to reach the gel stage.

Such extended curing times are however not acceptable for certain applications, for example medical or surgical use, where it is desired to form the gel quickly in situ e g. on a human or animal body.

U.S. Pat. No. 4 072 635 describes a silicone gel composition that can be cured in 10 seconds on an electronic encapsulating line and which has a pot life of at least 16 hours for use in making orthopaedic gel pads. The composition described and claimed has the same limitations on catalyst level, amount of silicon-bonded hydrogen in (2), ratio of vinylsiloxy units in (1) over silicon-bonded hydrogen atoms in (2) and molecular weight of (1) as for G.B. Specification 849 885 mentioned above. The average formulae of (1) and (2) are described as (1) an organosiloxane having a viscosity of from 10 to 10,000 cS at 25° C. and being a copolymer consisting essentially of units of the formula R$_2$ViSiO$_{0.5}$, RViSiO, R$_2$SiO and CH$_3$R$_2$SiO$_{0.5}$, where each R is individually selected from the group consisting of methyl and phenyl groups and Vi represents a vinyl group, at least 0.5 molar percent of the units in said copolymer being R$_2$ViSiO$_{0.5}$ units and RViSiO units where the terminal groups are at least 50 mole percent ViR$_2$SiO$_{0.5}$ units and may have as the rest of the total terminal units CH$_3$R$_2$SiO$_{0.5}$ units; (2) a liquid hydrogen siloxane of the average general formula XRCH$_3$SiO(R$_2$SiO)$_n$(RHSiO)$_m$SiCH$_3$Rx, where each R is as above defined and X is selected from the group consisting of H and R, no more than 25 molar percent of the total R groups in (1) and (2) being phenyl, and n and m have such average values that the viscosity of the hydrogen siloxane is no more than 10,000 cS at 25° C. and m is at least 1. The gel composition as described in the above mentioned specification is exemplified as curing in 10 seconds at 125° C. in one case and 60 minutes at 125° C. in another.

Such curing times, though shorter than those required according to the G.B. Specification, are still unsatisfactory with regard to the above mentioned medical or surgical applications, especially for applications where curing at body temperature is desired.

It is known that the curing times can be decreased by increasing the amount of hydrogen siloxane as described in U.S. Pat. Specification 4 072 635, but this results in a reaction product which is elastomeric, e.g. higher tear strength and shore hardness and not gel-like in nature.

Gel properties are retained by curing a composition according to G.B. Patent Specification 1 582 081 which describes a gel comprising a crosslinked polydimethylsiloxane prepared by mixing, (a) certain methylphenylvinylsiloxy end-blocked polydimethylsiloxanes; (b) a sufficient amount of certain dimethylhydrogensiloxy end-blocked polydimethylsiloxanes to provide an effective viscosity for (a) of from 4.5 to 30 Pa.s at 25° C.; (c) certain polydimethylsiloxanes having an average of at least three silicon-bonded hydrogen atoms per molecule, providing a ratio of total silicon-bonded hydrogen atoms to vinyl radicals in the composition of from 0.3:1 to 0.74:1 and (d) a catalytic amount of a compatible platinum catalyst. The gel can be cured according to the specification by allowing it to set at room temperature or it can be cured by heating it at a temperature of from 100° to 200° C. for 10 to 60 minutes. All examples give curing times of 20 minutes at 160° C. or 30 minutes at 150° C. These curing conditions are still not satisfactory for the above-mentioned applications.

We have now found that by using a certain mixture of hydrogen silicon compounds in specified ratios and organosiloxanes having alkenyl groups, a faster cure can be achieved at body or room temperature whilst retaining gel properties in the cured product.

This invention accordingly provides a siloxane gel-forming composition comprising the product obtained by mixing (A) a polydiorganosiloxane having on average two silicon-bonded alkenyl groups per molecule, said alkenyl group having from 2 to 6 carbon atoms and no silicon atom having more than one alkenyl group bonded thereto, the remaining silicon-bonded organic groups being selected from alkyl and aryl groups, said polydiorganosiloxane having a viscosity at 25° C. of from 50 to 10,000 mm$^2$/s, (B) a hydrosilicon compound having at least 3 silicon-bonded hydrogen atoms per molecule and consisting essentially of RHSiO—groups, R$_2$XSiO$_{\frac{1}{2}}$ groups and optionally R$_2$SiO— groups and having a viscosity at 25° C. of no more than 1000 mm$^2$/s, wherein R denotes an alkyl or aryl group having no more than 8 carbon atoms, and X denotes H or R, (C) a diorgano-hydrogensiloxy-terminated polydiorganosiloxane, having a viscosity of from 1 to 200 mm$^2$/s, wherein the organic substituents are alkyl or aryl groups having no more than 8 carbon atoms and (D) a catalyst for the reaction of ≡SiH groups with ≡Si-Alkenyl groups, the proportion of (A), (B) and (C) being such that for every alkenyl group in (A), there are present from 3 to about 20 silicon-bonded hydrogen atoms provided by (B) and (C) combined, the percentage of silicon-bonded hydrogen atoms provided by (C) (RH(C)) not being less than the value given by the formula $$RH(C) = 81.36 - (3.6 \times RHAlk)$$

wherein RHAlk is the ratio of the number of SiH groups in (B) and (C) combined to the number of Si-Alkenyl groups in (A) provided RH(C) is within the range of from 10% to 80%.

Polydiorganosiloxane (A) for use in the present invention has on average two silicon-bonded alkenyl groups per molecule, each alkenyl group being bonded to a different silicon atom. The polydiorganosiloxane (A) is a substantially linear polymer, although a small amount of branching may be present Preferably the alkenyl groups are attached to silicon atoms which are distant from each other in the molecule, and most preferably they are attached to the terminal silicon atoms of the siloxane chain. The alkenyl groups have a maximum of 6 carbon atoms and may be for example vinyl, allyl or hexenyl groups, although preferably they are vinyl groups. The remaining organic substituents of polydiorganosiloxane (A) are selected from alkyl and aryl groups, preferably alkyl groups having no more than 8 carbon atoms or phenyl groups. Examples of such remaining substituents are methyl, ethyl, propyl, isobutyl and phenyl Particularly preferred are those polydiorganosiloxane compounds where at least 50%, most preferably substantially all, of the remaining organic substituents are methyl groups Polydiorganosiloxane (A) has a viscosity at 25° C. of from 50 to 10,000 mm$^2$/s. The preferred viscosity range for polydiorganosiloxane (A) is from 100 to 1000 mm$^2$/s at 25° C. A polydiorganosiloxane with a viscosity above 10,000 mm$^2$/s would be difficult to use at room temperature where it needs to be mixed with the other components for the reaction Preferably the viscosity is chosen such that the composition is readily flowable prior to curing and can be dispensed easily from a container, for example a pressurised pack Polydiorganosiloxanes (A) are well known in the art and many are commercially available. They may be prepared for example by equilibrating in the presence of a mild catalyst, e.g. toluene sulphonic acid or acid treated clay, cyclic siloxanes with low molecular weight vinyl substituted end-blockers, which are produced by hydrolysing the appropriate chlorosilanes, e.g. vinyldiorganochlorosilane with diorganodichlorosilanes.

The hydrosilicon compound (B) for use in the invention is an organosiloxane, having at least 3 silicon-bonded hydrogen atoms per molecule. These hydrogen atoms may be located at terminal siloxane units as well as at siloxane units in the polymer chain, or they may be located only within the siloxane chain This hydrosilicon compound is essentially composed of units of the general formula RHSiO— groups, R$_2$XSiO$_{178}$ groups and optionally R$_2$SiO groups, wherein R an X are as defined above. The hydrosilicon compound (B) is a linear siloxane polymer, which may consist of units of the formula RHSiO— and R$_3$SiO$_{\frac{1}{2}}$ and/or R$_2$HSiO$_{\frac{1}{2}}$ or, more preferably, it may consist of R$_2$SiO—, RHSiO— and R$_3$SiO$_{\frac{1}{2}}$ and/or R$_2$HSiO$_{178}$ units most preferred are hydrosilicon compounds wherein not more than 50% of the units have silicon-bonded hydrogen atoms The viscosity of hydrosilicon compound (B) should not exceed 1000 mm$^2$/s at 25° C., viscosities below 500 mm$^2$/s being preferred to facilitate mixing with the other components of the composition. Most preferably the viscosity is less than 50 mm$^2$/s at 25° C. The hydrosilicon compounds (B) are well known in the art, and may be produced according to known methods. One such method consists of equilibrating a hydrogen cyclopolysiloxane with a cyclic organopolysiloxane, e.g. polydimethylcyclosiloxane and triorganosiloxy end-blocking compounds.

The diorganohydrogensiloxy-terminated polydiorganosiloxane (C) consists of diorganosiloxy units and diorgano hydrogen siloxy units. The organic substituents are alkyl or aryl groups having no more than 8 carbon atoms, preferably methyl or phenyl. Compound (C) has a viscosity of from 1 to 200 mm$^2$/s, preferably from 5 to 50 mm$^2$/s. This compound will react in the gel forming composition via its endgroups only.

Component (D) of the composition of this invention is a catalyst for the reaction of ≡SiH groups with ≡Si-Alkenyl groups. Such catalysts are generally group VIII metals or complexes or compounds thereof. Preferably component (D) is a platinum compound or complex This component is effective in catalysing the addition reaction between the alkenyl groups in (A) and the silicon-bonded hydrogen atoms in (B) and (C). The addition reaction between SiH groups and unsaturated aliphatic groups is well known in the art of organosilicon chemistry as are a variety of platinum-based catalysts for the reaction. Such catalysts are well documented in the art and include chloroplatinic acid, platinum acetylacetonate, complexes of platinous halides with unsaturated compounds such as ethylene, propylene, organovinylsiloxanes and styrene, hexamethyldiplatinum, PtCl$_2$.PtCl$_3$ and Pt(CN$_3$). The preferred platinum catalysts are complexes of platinum compounds and vinyl siloxanes e.g. those formed by the reaction of chloroplatinic acid and divinyltetramethyl disiloxane. Sufficient of the catalyst should be employed to provide a homogenous and effective cure of the composition. The preferred proportion of platinum catalyst is usually that which will provide from about 1 to about 40 parts by weight of Pt per million parts of the combined weights of (A), (B) and (C).

The value of RHAlk, i.e. the ratio of the number of silicon-bonded hydrogen atoms in (B) and (C) combined to the number of silicon bonded alkenyl groups in (A), is between 3:1 and about 20:1. If the ratio is lower insufficient silicon-bonded hydrogen atoms are available to react with the alkenyl groups in (A), if the value is higher than 20 no additional benefit is observed. Preferably the RHAlk has a value of from 3 to 7, and most preferably lies in the range from 3 to 5. When a ratio of at least 3 is chosen the reaction time for the gel is greatly reduced and gel formation can occur within less than 60 seconds for certain formulations. The curing time is also dependent on the amount of catalyst in the mixture and on the specific type of Components (B) and (C) which are used. If RHAlk has a value of at least 3 the gel formation occurs within 4 minutes for most formulations.

In order to obtain a cured product which has the physical properties of a gel, it is important that the percentage of silicon-bonded hydrogen groups, provided by Component (C) should be such that RH(C) has a value which is at least equal to $$RH(C) = 81.36 - (3.6 \times RHAlk)$$

wherein RH(C) is the percentage of all silicon-bonded hydrogen atoms in the reaction mixture attributed to Component (C), and RHAlk is the ratio of the number of silicon-bonded hydrogen atoms in (B) and (C) combined to the number of silicon bonded alkenyl groups in (A). If the value of RH(C) is lower, a product is obtained which has physical properties which are more closely related to those of elastomers. Increasing the value of RH(C) above that given by the above formula results in relatively softer gels. Such increase, however, extends the cure time of the composition. It is therefore preferred in most applications that RH(C) has a value the same as or approximating that obtained by application of the formula. For the preferred ratio of RHAlk described above RH(C) has a value of at least 56.16 (RHAlk = 7) or at least 74.16 (RHAlK = 3). If RH(C) is below 10%, and thus more than about 90% of the total number of silicon-bonded hydrogen atoms are provided by Component (B) the cured product is elastomeric. If RH(C) is above 90%, and thus less than 10% of the total number of SiH groups is provided by Component (B) the product remains liquid. It is preferred that RH(C) is from 20% to 80% whereupon cure of the composition to a gel can occur in about 15 minutes or less at 25° C.

The gel-forming compositions of the invention can be prepared by simply mixing the individual components (A) to (D) in any order, Generally the compositions will cure to the desired gel product at temperatures of about 25° C. If desired, however, curing may be accelerated by exposure to elevated temperatures e.g. 30° to 80° C. In order to maintain the compositions in the uncured state prior to use, for example during storage or transportation, they may be packaged in two or more parts. A first part may comprise at least part of Component (A) together with Component (D), while a second part may comprise Components (B) and (C) together with any remainder of component (A). These packages can take any suitable form, for example bottles, sachets or pressurised packs, e.g. aerosol cans. The contents of the packages are mixed together in predetermined ratios prior to their use, for example by manual mixing or by being dispensed via a mixing valve from a can-in-can or a can-upon-can system. Such systems are known in the art and are described e.g. in G.B. Patent Specification 2 185 750.

If desired, other ingredients may be present in the gel-forming composition. They may be added per se or premixed with one or more of the other components. Such additional ingredients include colorants and pharmaceutically active materials, e.g. antiseptics, antibacterial agents, antifungal agents and growth factors i.e. agents for the promotion of skin growth.

The gel-forming compositions of the invention are useful in the preparation of medical prostheses, e.g. mammary prostheses. They are also useful in the formation of surgical dressings where their short curing time renders them suitable for in situ application, e.g. on burns or other wounds. Another advantage of the gels of this invention is that there is no limit to the surface area one wishes to cover with a continuous layer, which is more difficult with a prior art pre-cured gel sheets.

There now follows a number of examples, which illustrate the invention All parts and percentages are given by weight unless otherwise specified, and Me and Vi denote respectively methyl and vinyl groups.

EXAMPLE 1-4 x parts of (A) a dimethylvinylsiloxy-endblocked polydimethylsiloxane polymer, having a viscosity of 450 mm$^2$/s at 25° C., were mixed with y parts of (B) a copolymer of methylhydrogensiloxy units and dimethylsiloxy units, endblocked with trimethylsilyl groups and having an average viscosity of about 4-6 mm$^2$/s at 25° C. and having on average 0.7 to 0.8% of H per molecule, z parts of (C) a dimethylhydrogensiloxy-endblocked polydimethylsiloxane, having an average viscosity of 10 mm$^2$/s at 25° C. and 0.12 parts of (D) a Pt complex, which is the reaction product of chloroplatinic acid and a vinylsiloxane. The RHAlk values ranged from 3 to 10, and the RH(C) value from 50 to 80. The mixture was allowed to react and cure at room temperature to form a gel. The gel was tested for penetration according to the test method described below. The values for x, y, z, RHAlk, RH(C), curing time (in seconds), and penetration (in 0.1 mm) are given in Table I.

TABLE I

| x | y | z | RHAlk | RH(C) | Curing Time | Penetration |
|---|---|---|---|---|---|---|
| 47.31 | 2.02 | 50.55 | 10 | 80 | 60 | 275 |
| 68.98 | 1.47 | 29.43 | 4 | 80 | 150 | 230 |
| 74.76 | 1.20 | 23.92 | 3 | 80 | 220 | 230 |
| 64.40 | 5.92 | 29.63 | 7 | 50 | 30 | 68 |

Penetration test method

A penetrometer from Universal, Precision Scientific, Chicago was equipped with an aluminium rod and an aluminium head, having a brass tip of 3/16 inch long and ¼ inch in diameter. The rod and head together weighed 19.5 g and the head itself 4.30 g. The cured gel sample was stabilised at room temperature (25° C.) for 30 minutes and placed under the penetrometer head, with the head touching the surface without making an indentation. The trigger on the meter was released for 5 seconds and the penetration depth measured with the depth gauge. The dial reads the penetration value in 0.1 mm values. A gel having a penetration value of 60 or more is regarded as a satisfactory gel.

EXAMPLE 5

75.11 parts of (A) of Examples 1-4 was mixed with 24.16 parts of (C), 0.12 parts of (D) the Pt complex and 0.61 parts of (B') a trimethylsiloxy-endblocked polymethylhydrogen siloxane, having an average viscosity of 22 mm$^2$/s at 25° C. and having on average 1.5% H atoms per molecule. The RHAlk value of the mixture was 3, RH(C) was 80 and the mixture took 175 seconds to cure to a gel with a penetration value of 70.

That which is claimed is:

1. A siloxane gel-forming composition comprising the product obtained by mixing (A) a polydiorganosiloxane having on average two silicon-bonded alkenyl groups per molecule, said alkenyl group having from 2 to 6 carbon atoms and no silicon atom having more than one alkenyl group bonded thereto, the remaining silicon-bonded organic groups being selected from alkyl and aryl groups, said polydiorganosiloxane having a viscosity at 25° C. of from 50 to 10,000 mm$^2$/s, (B) a hydrosilicon compound having at least 3 silicon-bonded hydrogen atoms per molecule and consisting essentially of RHSiO— groups, $R_2XSiO_{\frac{1}{2}}$ groups and optionally $R_2SiO$— groups and having a viscosity at 25° C. of no more than 1000 mm$^2$/s, wherein R is selected from the group consisting of alkyl and aryl groups having no more than 8 carbon atoms, and X is selected from H and R, (C) a diorganohydrogensiloxy-terminated polydiorganosiloxane, having a viscosity of from 1 to 200 mm$^2$/s, wherein the organic substituents are selected from alkyl and aryl groups having no more than 8 carbon atoms and (D) a catalyst for the reaction of ≡SiH groups with ≡SiAlkenyl groups, the proportion of (A), (B) and (C) being such that for every alkenyl group in (A), there are present from 3 to about 20 silicon-bonded hydrogen atoms provided by (B) and (C) combined, the percentage of silicon-bonded hydrogen atoms provided by (C) (RH(C)) not being less than the value given by the formula $$RH(C) = 81.36 - (3.6 \times RHAlk)$$

wherein RHAlk is the ratio of the number of SiH groups in (B) and (C) combined to the number of Si-Alkenyl groups in (A) provided RH(C) is within the range of from 10% to 90%.

2. A siloxane gel-forming composition according to claim 1 wherein (B) and (C) combined provide from 3 to 5 silicon-bonded hydrogen atoms for every silicon-bonded alkenyl group in (A).

3. A siloxane gel-forming composition according to claim 1 wherein RH(C) is substantially equal to 81.36 — (3.6 × RHAlk).

4. A siloxane gel-forming composition according to claim 1 wherein (A) is a dimethyl vinyl siloxy endblocked polydimethylsiloxane.

5. A siloxane gel-forming composition according to claim 1 wherein (B) is a copolymer having no more than 50% of all siloxy units with a silicon-bonded hydrogen atom.

6. A siloxane gel-forming composition according to claim 1 wherein (B) has a viscosity of less than 50 mm$^2$/s at 25° C.

7. A siloxane gel-forming composition according to claim 1 wherein (C) has a viscosity of from 5 to 50 mm$^2$/s at 25° C.

8. A siloxane gel-forming composition according to claim 1 wherein (D) is selected from platinum compounds and platinum complexes.

9. A non-friable siloxane gel which is the product obtained by curing a composition as claimed in claim 1.

10. A medical or surgical gel dressing comprising a non-friable siloxane gel as claimed in claim 9.

11. A medical or surgical gel dressing as claimed in claim 10 wherein the gel also comprises a pharmaceutically active material.

12. A medical prostheses containing a siloxane gel as claimed in claim 9.

* * * * *